(12) United States Patent
Lee

(10) Patent No.: US 7,416,566 B2
(45) Date of Patent: Aug. 26, 2008

(54) DYEING COMPOSITION FOR HAIR

(75) Inventor: Byung-Jun Lee, Bucheon-Si (KR)

(73) Assignees: Kirin Cosmetics Co., Ltd. (KR); Beauty Master Inc., Compton, CA (US)

( * ) Notice: Subject to any disclaimer, the term of this patent is extended or adjusted under 35 U.S.C. 154(b) by 345 days.

(21) Appl. No.: 11/253,836

(22) Filed: Oct. 19, 2005

(65) Prior Publication Data

US 2007/0074355 A1 Apr. 5, 2007

(30) Foreign Application Priority Data

Sep. 30, 2005 (KR) .................. 10-2005-0092330

(51) Int. Cl.
*A61Q 5/10* (2006.01)
(52) U.S. Cl. .................. 8/405; 8/406; 8/408; 8/435; 8/646
(58) Field of Classification Search .................. 8/405, 8/406, 408, 415, 435, 646
See application file for complete search history.

(56) References Cited

U.S. PATENT DOCUMENTS

| 6,648,925 | B1 * | 11/2003 | Mayer et al. | .................. 8/405 |
| 2003/0167578 | A1 * | 9/2003 | Naumann et al. | .............. 8/405 |

* cited by examiner

*Primary Examiner*—Eisa B Elhilo
(74) *Attorney, Agent, or Firm*—Cantor Colburn LLP

(57) ABSTRACT

Disclosed herein is a hair dyeing composition. The composition induces swelling of hair to expand the cortex by the use of arginine, which is a constituent ingredient of hair, and as a result, effectively allows a colorant to infiltrate into the cuticle, thereby increasing the dyeing rate. Therefore, the composition can markedly decrease the dyeing time to 1~5 minutes from 20~30 minutes required in conventional hair dyeing compositions. In addition, the combined effects of aloe vera gel, ceramide and hair keratin enables prevention of damage to the hair during dyeing.

1 Claim, No Drawings

DYEING COMPOSITION FOR HAIR

BACKGROUND OF THE INVENTION

1. Field of the Invention

The present invention relates to a hair dyeing composition, and more particularly to a hair dyeing composition which induces swelling of hair to expand the cortex by the use of arginine, which is a constituent amino acid of hair, and as a result, effectively allows a colorant to infiltrate into the cuticle, thereby shortening the dyeing time to reduce damage to the hair caused by chemical factors, and which can prevent damage of the hair due to the combined effects of aloe vera gel, ceramide and hair keratin during dyeing.

2. Description of the Related Art

Hair dyeing is an artistic act of human desire to seek beauty by applying science to the color of natural hair. Hair dying is generally performed to return grey hair to an original hair color, alter an original hair color into more attracting color tone or brightness or exhibit hair decorative effects by coloring natural hair with an artificial colorant, and to restore an original natural hair color by coloring already dyed hair or already discolored hair with an artificial colorant.

Hair dyeing agents (so-called "hair dyestuffs") are largely classified into three groups, i.e., temporary hair dyeing agents, semi-permanent hair dyeing agents and permanent hair dyeing agents, depending on the characteristics of particular dyes used and color fixation period of the hair. Of these, permanent hair dyeing agents are most widely used at present. Examples of dyes used in the permanent hair dyeing agents include vegetable dyes, metallic dyes, compound dyes, and oxidative dyes (organic synthetic dyes). Oxidative dyes are most widely used.

As permanent hair dyeing agents using oxidative dyes, there are currently used double-formulations consisting of a first functional agent containing an oxidative dye precursor, a coupler and an alkalizing agent, and a second functional agent containing an oxidizing agent. More specifically, the first functional agent contains a colorless or substantially colorless oxidative dye precursor, such as an aromatic amino compound or a phenol derivative, a coupler and an alkalizing agent, and the second functional agent contains an oxidizing agent, such as hydrogen peroxide.

The oxidative dye precursor and the coupler used herein are colorless or pale compounds, and are polymerized in the presence of an oxidizing agent to form a colorant, which is a coloring compound capable of exerting adequate hair dyeing power on the hair. As the oxidative dye precursor and the coupler, meta-phenylenediamine, meta-aminophenol, meta-diphenol and specific heterocyclic compounds are widely used. Ammonia is widely used as the alkalizing agent because it is highly volatile and leaves no residue. Ammonia is associated with problems of unpleasant odor and irritation to parts of the human body, such as eyes. To solve these problems, monoethanolamine and monoisopropanolamine are used instead of ammonia.

When a mixture of the first and second functional agents is applied to the hair during dyeing, the alkalizing agent contained in the first functional agent decomposes the oxidizing agent contained in the second functional agent to generate oxygen. The oxygen decomposes melanin of the hair to bleach the hair. At the same time, an oxidative dye consisting of the oxidative dye precursor and the coupler contained in the first functional agent is polymerized by the oxidative power of the oxidizing agent in the hair to form a colorant. The colorant thus formed is deposited on the cuticle and dyes the hair.

In the hair dyeing agents using general oxidative dyes, the alkalizing agent swells the epidermis of the hair and infiltrates the colorant into the hair, thus advantageously improving hair dyeing effects. However, since the alkalizing agent damages the hair and readily decomposes keratin proteins present on the hair surface, the hair feels bad to the touch after dyeing. Particularly, since conventional hair dyeing agents using oxidative dyes require long periods of time for dyeing, the hair is exposed to alkalizing agents for a long time, causing great damage to the hair.

SUMMARY OF THE INVENTION

Therefore, it is one object of the present invention to provide a hair dyeing composition which induces rapid swelling of hair to expand the cortex, and as a result, effectively allows a colorant to infiltrate the cuticle, thereby shortening the dyeing time to reduce damage to the hair caused by chemical factors.

It is another object of the present invention to provide a hair dyeing composition that makes the hair wet and glossy and can protect the scalp by providing potent moisturizing effects to damaged and roughened hair after dyeing.

In accordance with one aspect of the present invention for achieving the above objects, there is provided a hair dyeing composition comprising a first functional agent containing an oxidative dye and an alkalizing agent and a second functional agent containing an oxidizing agent wherein the first functional agent further contains arginine for increasing the dyeing rate in an amount of 1.0~5.0% by weight, based on the weight of the first functional agent.

Preferably, the first functional agent further contains at least one additive selected from aloe vera gel, ceramide and hair keratin to protect the hair from damage. It is preferred that the first functional agent contains all of the additives. Preferably, the first functional agent contains 1.0~10.0% by weight of aloe vera gel, 0.1~1.0% by weight of ceramide and 0.3~1.0% by weight of hair keratin, based on the weight of the first functional agent.

DESCRIPTION OF THE PREFERRED EMBODIMENTS

Hereinafter, the present invention will be explained in more detail.

A hair dyeing composition of the present invention comprises a first functional agent containing an oxidative dye and an alkalizing agent and a second functional agent containing an oxidizing agent wherein the first functional agent further contains arginine for increasing the dyeing rate.

The arginine contained in the first functional agent is a constituent amino acid of hair. The dyeing composition comprising arginine in the first function agent according to the present invention induces rapid swelling of hair upon hair dyeing to expand the cortex, and as a result, assists in effective infiltration of a colorant into the cuticle. Consequently, the dyeing composition of the present invention can considerably decrease the dyeing time to 1~5 minutes when compared to the use of conventional hair dyeing agents, and thus enables expression of desired colors while minimizing damage to hair.

The first functional agent preferably contains arginine in an amount of 1.0~5.0% by weight, based on the weight of the first functional agent. When the content of the arginine is less than 1.0% by weight, adsorption and infiltration properties of the arginine are poor, causing the problem of insufficient improvement in dyeing rate. Meanwhile, when the content of the arginine exceeds 5.0% by weight, adsorption and infiltration properties of the arginine are similar to each other and thus the dyeing rate is not greatly increased. Accordingly, the content of the arginine preferably falls within the range defined above.

Although the hair dyeing composition of the present invention containing arginine is used to dye hair, hair damage may be inevitable due to inherent characteristics of dyeing agents. In view of this problem, the first functional agent further contains at least one additive selected from aloe vera gel, ceramide and hair keratin to protect the hair from damage. Preferably, the first functional agent further contains all of the additives.

The aloe vera gel used herein serves to maintain the moisturizing power of the hair at a constant level, the ceramide serves to restore or enhance the cell binding force of the hair to restore damaged hair, and the hair keratin serves to recover the strength, elasticity and flexibility of hair damaged by dyeing. The ceramide and the hair keratin are constituent ingredients of hair. When the ceramide and the hair keratin are combined with aloe vera gel in the first functional agent, they make the hair wet and glossy and can protect the scalp by providing potent moisturizing effects to damaged and roughened hair due to the combined effects after dyeing, enabling rapid recovery of damaged hair.

Preferably, the first functional agent contains 1.0~10.0% by weight of aloe vera gel, 0.1~1.0% by weight of ceramide and 0.3~1.0% by weight of hair keratin, based on the weight of the first functional agent.

When the aloe vera gel is present in an amount of less than 1.0% by weight, it does not provide sufficient moisturizing power to the hair, making the hair dry. On the other hand, when the aloe vera gel is present in an amount exceeding 10.0% by weight, dyeability may be deteriorated.

Accordingly, the content of the aloe vera gel preferably falls within the range defined above.

When the ceramide is present in an amount of less than 0.1% by weight, ability to restore or enhance cell binding force of damage hair is poor, making it difficult to restore glossy hair. Meanwhile, when the ceramide is present in an amount exceeding 1.0% by weight, it forms a lipoprotein complex with neighboring proteins and enters the cortex, deteriorating the dyeability of the colorant. Accordingly, the content of the ceramide preferably falls within the range defined above.

The hair keratin is extracted from human hair. When the hair keratin is present in an amount of less than 0.3% by weight, ability to restore the strength, elasticity and flexibility of damaged hair caused by dyeing is poor. Meanwhile, when the hair keratin is present in an amount exceeding 1.0% by weight, an excessive amount of the hair keratin does not contribute to further improvement in strength, elasticity and flexibility of damaged hair caused by dyeing. Accordingly, the content of the hair keratin preferably falls within the range defined above.

In addition to the above-mentioned ingredients of the first functional agent, the hair dyeing composition of the present invention may further comprise an oxidative dye and an alkalizing agent used in common hair dyeing compositions for oxidative dyeing within allowable content ranges.

It is common that the oxidative dye consists of an oxidative dye precursor and a coupler. The oxidative dye precursor can be selected from o-aminophenol, p-aminophenol, toluene-2, 5-diamine HCl, p-phenylenediamine HCl, toluene-2,5-diamine, p-phenylenediamine, p-methylaminophenol sulfate, o-aminophenol sulfate, p-aminophenol sulfate, toluene-2,5-diamine sulfate, and p-phenylenediamine sulfate. The coupler can be selected from 2-methyl-5-hydroxyethyl aminophenol, p-amino-o-cresol, m-aminophenol, 2,4-diaminophenoxyethanol HCl, m-phenylenediamine HCl, m-phenylenediamine, N-methyl-p-phenylenediamine, p-amino-o-cresol sulfate, 4-ethoxy-m-phenylenediamine sulfate, m-phenylenediamine sulfate, α-naphthol, resorcinol, and 2-methylresorcinol.

The hair dyeing composition of the present invention may further comprise a direct dye ordinarily employed in the art other than the oxidative dyes. Examples of suitable direct dyes include arianol dyes, p-nitro-o-phenylenediamine, nitro-p-phenylenediamine, 2-amino-4-nitrophenol, 2-amino-5-nitrophenol, nitro-p-phenylenediamine HCl, picramic acid, and other vegetable dyes, such as henna.

The alkalizing agent can be selected from ammonia, monoethanolamine and aminomethylpropanol used commonly in the art.

In addition to the oxidative dye and the alkalizing agent, the first functional agent may further contain a fatty acid alcohol selected from cetyl alcohol, oleyl alcohol and behenyl alcohol, a surfactant selected from polyoxyethylene cetyl ether and polyoxyethylene stearyl ether, a thickener selected from carboxyvinyl polymers, hydroxyethyl cellulose, guar gum and xanthan gum, a humectant selected from glycerol, 1,3-butylene glycol and polyethylene glycol, or a fragrance. For the desired viscosity, water can be further contained in the first functional agent.

The second functional agent that is mixed with the first functional agent may contain additives selected from constituent ingredients of general hair dyeing compositions comprising hydrogen peroxide as a main ingredient. For example, the second functional agent may contain a hydrogen peroxide solution, a fatty acid alcohol, a surfactant and water. If necessary, the second functional agent may further contain other additives used commonly in the art.

The hair dyeing composition comprising the first and second functional agents can be formulated into various forms, such as lotions, creams, pastes, gels, aerosols and aerosol foams. A mixture of the first functional agent and the second functional agent is applied to the hair. One to five minutes after application to the hair, the mixture is shampooed and rinsed with water to complete hair dyeing.

The present invention will now be described in more detail with reference to the following examples. However, these examples are given for the purpose of illustration and are not to be construed as limiting the scope of the invention.

EXAMPLES 1 TO 6 AND COMPARATIVE
EXAMPLE 1 TO 6

Polyquaternium 10 was dissolved in purified water at 50° C., and then EDTA-2NA, propylene glycol, Polyquaternium 7, ammonium thioglycolate, ethanolamine thioglycolate, L-arginine, glycerin and DL-panthenol were added thereto. The mixture was dissolved by heating to 80° C. To the resulting solution were added p-phenylenediamine, p-aminophenol, m-aminophenol, p-amino-O-cresol, m-phenylenediamine HCl, and resorcinol. After the mixture was dissolved, a solution of cetyl alcohol, ceramide, lanolin oil, mineral oil, oleyl alcohol, behenyl alcohol and polyoxyethylene cetyl ether at 80° C. was added thereto to obtain an emulsion. Thereafter, Carbomer, monoethanolamine, a fragrance, aloe vera gel and hair keratin were sequentially added to the emulsion, and cooled to prepare first functional agents. The ingredients used to prepare the first functional agents had the compositions (wt %) shown in Tables 1 and 2.

Separately, Polyquaternium 10, propylene glycol, phosphoric acid, and sodium pyrophosphate were dissolved in purified water at 50° C. To the solution was added a solution of cetyl alcohol, polyoxyethylene cetyl ether, phenacethin, and steartrimonium chloride at 80° C. to obtain an emulsion. The emulsion was cooled to 45° C. Finally, a fragrance and a hydrogen peroxide solution (35%) were added to the cooled emulsion to prepare second functional agents as viscous oxidizing agents. The ingredients used to prepare the second functional agents had the compositions (wt %) shown in Table 3.

TABLE 1

| Raw Material | Ex. 1 Content (W/W %) | Ex. 2 Content (W/W %) | Ex. 3 Content (W/W %) | Comp. Ex. 1 Content (W/W %) | Comp. Ex. 2 Content (W/W %) | Comp. Ex. 3 Content (W/W %) |
|---|---|---|---|---|---|---|
| Purified water | to 100 | to 100 | to 100 | to 100 | to 100 | to 100 |
| Polyquaternium 10 | 0.50 | 0.50 | 0.50 | 0.50 | 0.50 | 0.50 |
| EDTA-2Na | 2.00 | 2.00 | 2.00 | 2.00 | 2.00 | 2.00 |
| Propylene glycol | 2.00 | 2.00 | 2.00 | 2.00 | 2.00 | 2.00 |
| Polyquaternium 7 | 1.00 | 1.00 | 1.00 | 1.00 | 1.00 | 1.00 |
| Ammonium thioglycolate | 0.20 | 0.20 | 0.20 | 0.20 | 0.20 | 0.20 |
| Ethanolamine thioglycolate | 1.00 | 1.00 | 1.00 | 1.00 | 1.00 | 1.00 |
| L-Arginine | 3.00 | 1.00 | 5.00 | — | 0.50 | 8.00 |
| Glycerin | 1.00 | 1.00 | 1.00 | 1.00 | 1.00 | 1.00 |
| DL-Panthenol | 0.50 | 0.50 | 0.50 | 0.50 | 0.50 | 0.50 |
| p-Phenylenediamine | 1.00 | 1.00 | 1.00 | 1.00 | 1.00 | 1.00 |
| p-Aminophenol | 0.08 | 0.08 | 0.08 | 0.08 | 0.08 | 0.08 |
| m-Aminophenol | 0.36 | 0.36 | 0.36 | 0.36 | 0.36 | 0.36 |
| p-Amino-O-cresol | 0.60 | 0.60 | 0.60 | 0.60 | 0.60 | 0.60 |
| m-Phenylenediamine HCl | 0.10 | 0.10 | 0.10 | 0.10 | 0.10 | 0.10 |
| Resorcinol | 0.80 | 0.80 | 0.80 | 0.80 | 0.80 | 0.80 |
| Cetyl alcohol | 3.80 | 3.80 | 3.80 | 3.80 | 3.80 | 3.80 |
| Ceramide | 1.00 | 1.00 | 1.00 | 1.00 | 1.00 | 1.00 |
| Lanolin oil | 2.00 | 2.00 | 2.00 | 2.00 | 2.00 | 2.00 |
| Mineral oil | 2.00 | 2.00 | 2.00 | 2.00 | 2.00 | 2.00 |
| Oleyl alcohol | 3.00 | 3.00 | 3.00 | 3.00 | 3.00 | 3.00 |
| Behenyl alcohol | 1.00 | 1.00 | 1.00 | 1.00 | 1.00 | 1.00 |
| Polyoxyethylene cetyl ether | 5.00 | 5.00 | 5.00 | 5.00 | 5.00 | 5.00 |
| Carbomer | 0.20 | 0.20 | 0.20 | 0.20 | 0.20 | 0.20 |
| Monoethanolamine | 5.00 | 5.00 | 5.00 | 5.00 | 5.00 | 5.00 |
| Fragrance | 0.10 | 0.10 | 0.10 | 0.10 | 0.10 | 0.10 |
| *Aloe vera* gel | 0.20 | 0.20 | 0.20 | 0.20 | 0.20 | 0.20 |
| Keratin | 1.00 | 1.00 | 1.00 | 1.00 | 1.00 | 1.00 |
| Total | 100.00 | 100.00 | 100.00 | 100.00 | 100.00 | 100.00 |

TABLE 2

| Raw Material | Ex. 4 Content (W/W %) | Ex. 5 Content (W/W %) | Ex. 6 Content (W/W %) | Comp. Ex. 4 Content (W/W %) | Comp. Ex. 5 Content (W/W %) | Comp. Ex. 6 Content (W/W %) |
|---|---|---|---|---|---|---|
| Purified water | to 100 | to 100 | to 100 | to 100 | to 100 | to 100 |
| Polyquaternium 10 | 0.50 | 0.50 | 0.50 | 0.50 | 0.50 | 0.50 |
| EDTA-2Na | 2.00 | 2.00 | 2.00 | 2.00 | 2.00 | 2.00 |
| Propylene glycol | 2.00 | 2.00 | 2.00 | 2.00 | 2.00 | 2.00 |
| Polyquaternium 7 | 1.00 | 1.00 | 1.00 | 1.00 | 1.00 | 1.00 |
| Ammonium thioglycolate | 0.20 | 0.20 | 0.20 | 0.20 | 0.20 | 0.20 |
| Ethanolamine thioglycolate | 1.00 | 1.00 | 1.00 | 1.00 | 1.00 | 1.00 |
| L-Arginine | 3.00 | 3.00 | 3.00 | 3.00 | 3.00 | 3.00 |
| Glycerin | 1.00 | 1.00 | 1.00 | 1.00 | 1.00 | 1.00 |
| DL-Panthenol | 0.50 | 0.50 | 0.50 | 0.50 | 0.50 | 0.50 |
| p-Phenylenediamine | 1.00 | 1.00 | 1.00 | 1.00 | 1.00 | 1.00 |
| p-Aminophenol | 0.08 | 0.08 | 0.08 | 0.08 | 0.08 | 0.08 |
| m-Aminophenol | 0.36 | 0.36 | 0.36 | 0.36 | 0.36 | 0.36 |
| p-Amino-O-cresol | 0.60 | 0.60 | 0.60 | 0.60 | 0.60 | 0.60 |
| m-Phenylenediamine HCL | 0.10 | 0.10 | 0.10 | 0.10 | 0.10 | 0.10 |
| Resorcinol | 0.80 | 0.80 | 0.80 | 0.80 | 0.80 | 0.80 |
| Cetyl alcohol | 3.80 | 3.80 | 3.80 | 3.80 | 3.80 | 3.80 |
| Ceramide | 0.50 | 0.1 | 1.00 | 0.05 | 2.00 | 1.00 |
| Lanolin oil | 2.00 | 2.00 | 2.00 | 2.00 | 2.00 | 2.00 |
| Mineral oil | 2.00 | 2.00 | 2.00 | 2.00 | 2.00 | 2.00 |

TABLE 2-continued

| Raw Material | Ex. 4 Content (W/W %) | Ex. 5 Content (W/W %) | Ex. 6 Content (W/W %) | Comp. Ex. 4 Content (W/W %) | Comp. Ex. 5 Content (W/W %) | Comp. Ex. 6 Content (W/W %) |
|---|---|---|---|---|---|---|
| Oleyl alcohol | 3.00 | 3.00 | 3.00 | 3.00 | 3.00 | 3.00 |
| Behenyl alcohol | 1.00 | 1.00 | 1.00 | 1.00 | 1.00 | 1.00 |
| Polyoxyethylene cetyl ether | 5.00 | 5.00 | 5.00 | 5.00 | 5.00 | 5.00 |
| Carbomer | 0.20 | 0.20 | 0.20 | 0.20 | 0.20 | 0.20 |
| Monoethanolamine | 5.00 | 5.00 | 5.00 | 5.00 | 5.00 | 5.00 |
| Fragrance | 0.10 | 0.10 | 0.10 | 0.10 | 0.10 | 0.10 |
| *Aloe vera* gel | 10.00 | 5.00 | 1.00 | 7.00 | 0.50 | 15.00 |
| Hair keratin | 0.70 | 1.00 | 0.30 | 1.00 | 2.00 | 0.10 |
| Total | 100.00 | 100.00 | 100.00 | 100.00 | 100.00 | 100.00 |

TABLE 3

| Raw Material | Content (W/W %) |
|---|---|
| Purified water | To 100.00 |
| Polyquaternium 10 | 0.18 |
| Propylene glycol | 1.50 |
| Phosphoric acid | 0.015 |
| Sodium pyrrophosphate | 0.01 |
| Cetyl alcohol | 1.25 |
| Polyoxyethylene cetyl ether | 0.80 |
| Phenacethin | 0.04 |
| Steartrimonium chloride | 0.30 |
| Fragrance | 0.1 |
| Hydrogen peroxide Solution, 35% | 17.00 |
| Total | 100.00 |

EXPERIMENTAL EXAMPLE 1

Each of the first functional agents and each of the second functional agents prepared in Examples 1 to 6 and Comparative Example 1 to 6 were mixed in a ratio of 1:1. The mixtures were applied to the hair of five human subjects. After the time indicated in Table 4 lapsed, the mixtures were washed away with a shampoo, and then the hair was dried. The color development in the hairs was judged by ten panelists who have worked in beauty-related professions for more than 10 years and scored based on the following criteria. 5: excellent, 4: good, 3: average, 2: poor, 1: very poor. The average values are shown in Table 4 below.

TABLE 4

| Example No. | 1 min. | 2 min. | 5 min. | 10 min. | 20 min. |
|---|---|---|---|---|---|
| Example 1 | 4.0 | 4.3 | 4.9 | 5.0 | 5.0 |
| Example 2 | 3.8 | 4.0 | 4.7 | 5.0 | 5.0 |
| Example 3 | 4.6 | 4.8 | 5.0 | 5.0 | 5.0 |
| Comparative Example 1 | 1.0 | 1.0 | 1.5 | 2.5 | 3.0 |
| Comparative Example 2 | 2.0 | 2.5 | 3.0 | 3.0 | 3.5 |
| Comparative Example 3 | 4.6 | 4.8 | 5.0 | 5.0 | 5.0 |
| Example 4 | 4.2 | 4.3 | 4.6 | 5.0 | 5.0 |
| Example 5 | 4.2 | 4.3 | 4.6 | 5.0 | 5.0 |
| Example 6 | 4.1 | 4.3 | 4.6 | 5.0 | 5.0 |
| Comparative Example 4 | 4.0 | 4.1 | 4.3 | 4.6 | 5.0 |
| Comparative Example 5 | 3.8 | 3.9 | 4.0 | 4.3 | 4.6 |
| Comparative Example 6 | 3.7 | 3.9 | 4.0 | 4.1 | 4.5 |

As can be seen from the data shown in Table 4, the hair dyeing agents prepared in Examples 1 to 6 showed good results 1~5 minutes after hair dyeing, whereas the conventional hair dyeing agents showed similar results 20~30 minutes after hair dyeing. Accordingly, the hair dyeing agents of the present invention can markedly shorten the hair dyeing time.

As evident from Table 4, the hair dyeing agents containing various arginine amounts (Examples 1 to 3) can markedly shorten the hair dyeing time when compared to the hair dyeing agent containing no arginine (Comparative Example 1) and the hair dyeing agents containing arginine outside the defined range (Comparative Examples 2 and 3).

EXPERIMENTAL EXAMPLES 2 TO 4

Each of the first functional agents and each of the second functional agents prepared in Examples 1 to 6 and Comparative Example 1 to 6 were mixed in a ratio of 1:1. The mixtures were applied to the hair of five human subjects. Five minutes after application, the mixtures prepared in Examples 1 to 6 were washed away with a shampoo, and then the hairs were dried. Thirty minutes after application, the mixtures prepared in Comparative Examples 1 to 6 were washed away with a shampoo, and then the hairs were dried. The glossiness and dyeability of the hairs were visually observed and the fastness and moisturization of the hairs were judged by ten panelists who have worked in beauty-related professions for more than 10 years, and scored based on the following criteria. 5: excellent, 4: good, 3: average, 2: poor, 1: very poor. The average values are shown in Table 5 below.

TABLE 5

| Example No. | Fastness | Dyeability | Moisturization | Glossiness |
|---|---|---|---|---|
| Example 1 | 4.0 | 4.8 | 4.0 | 4.5 |
| Example 2 | 4.0 | 4.6 | 4.0 | 4.5 |
| Example 3 | 4.0 | 4.8 | 4.0 | 4.5 |
| Comparative Example 1 | 3.0 | 3.0 | 4.0 | 3.5 |

TABLE 5-continued

| Example No. | Fastness | Dyeability | Moisturization | Glossiness |
|---|---|---|---|---|
| Comparative Example 2 | 3.2 | 3.3 | 4.0 | 3.6 |
| Comparative Example 3 | 4.0 | 4.5 | 4.0 | 4.5 |
| Example 4 | 4.0 | 4.5 | 4.5 | 4.2 |
| Example 5 | 4.0 | 4.5 | 4.5 | 4.0 |
| Example 6 | 4.0 | 4.5 | 4.3 | 4.5 |
| Comparative Example 4 | 3.8 | 4.1 | 3.7 | 3.0 |
| Comparative Example 5 | 4.0 | 3.0 | 3.5 | 3.8 |
| Comparative Example 6 | 3.2 | 2.8 | 3.7 | 3.8 |

As can be seen from the data shown in Table 5, the hair dyeing agents prepared in Examples 1 to 6 showed superior fastness, dyeability, moisturization and glossiness to those prepared in Comparative Examples 1 to 6 comprising the ingredients outside the defined content ranges.

Particularly, as evident from Table 5, the hair dyeing agents of Examples 4 to 6 containing various amounts of aloe vera gel, ceramide and hair keratin within the ranges defined above showed superior fastness, dyeability, moisturization and glossiness to those of Comparative Examples 1 to 6 comprising the ingredients outside the defined content ranges.

As apparent from the above description, the hair dyeing composition of the present invention induces swelling of hair to expand the cortex by the use of arginine, which is a constituent ingredient of hair, and as a result, effectively allows a colorant to infiltrate into the cuticle, thereby increasing the dyeing rate. Therefore, the hair dyeing composition of the present invention can markedly decrease the dyeing time to 1~5 minutes from 20~30 minutes required in conventional hair dyeing compositions. This decrease in dyeing time reduces damage to the hair caused by chemical factors. In addition, the combined effects of aloe vera gel, ceramide and hair keratin advantageously enables prevention of damage to the hair during dyeing.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A hair dyeing composition comprising a first functional agent containing an oxidative dye and an alkalizing agent and a second functional agent containing an oxidizing agent wherein the first functional agent further contains arginine for increasing the dyeing rate in an amount of 1.0~5.0% by weight, based on the weight of the first functional agent, and wherein the first functional agent contains 1.0~10.0% by weight of aloe vera gel, 0.1~1.0% by weight of ceramide and 0.3~1.0% by weight of hair keratin, based on the weight of the first functional agent.

* * * * *